(12) United States Patent
Kwon et al.

(10) Patent No.: US 12,099,057 B2
(45) Date of Patent: Sep. 24, 2024

(54) MULTIPLEX DETECTION OF BACTERIAL PATHOGENS VIA CELL WALL BINDING DOMAIN COMPLEXES

(71) Applicant: RENSSELAER POLYTECHNIC INSTITUTE, Troy, NY (US)

(72) Inventors: Seok-Joon Kwon, Niskayuna, NY (US); Jonathan Seth Dordick, Schenectady, NY (US); Domyoung Kim, Troy, NY (US); Jungbae Kim, Seoul (KR); Inseon Lee, Yongin (KR)

(73) Assignee: Rensselaer Polytechnic Institute, Troy, NY (US)

( * ) Notice: Subject to any disclaimer, the term of this patent is extended or adjusted under 35 U.S.C. 154(b) by 513 days.

(21) Appl. No.: 16/611,563

(22) PCT Filed: May 8, 2018

(86) PCT No.: PCT/US2018/031511
§ 371 (c)(1),
(2) Date: Nov. 7, 2019

(87) PCT Pub. No.: WO2018/208726
PCT Pub. Date: Nov. 15, 2018

(65) Prior Publication Data
US 2021/0148904 A1  May 20, 2021

Related U.S. Application Data

(60) Provisional application No. 62/667,998, filed on May 7, 2018, provisional application No. 62/647,292, filed on Mar. 23, 2018, provisional application No. 62/502,856, filed on May 8, 2017.

(51) Int. Cl.
| | |
|---|---|
| *G01N 33/543* | (2006.01) |
| *C12Q 1/26* | (2006.01) |
| *C12Q 1/6851* | (2018.01) |
| *C12Q 1/689* | (2018.01) |
| *G01N 33/569* | (2006.01) |

(52) U.S. Cl.
CPC ......... *G01N 33/54306* (2013.01); *C12Q 1/26* (2013.01); *C12Q 1/6851* (2013.01); *C12Q 1/689* (2013.01); *C12Y 101/03004* (2013.01); *G01N 33/56911* (2013.01)

(58) Field of Classification Search
CPC ....... G01N 33/54306; G01N 33/56911; G01N 33/54353; G01N 33/54313; G01N 33/58; C12Q 1/26; C12Q 1/6851; C12Q 1/689; C12Y 101/03004; C07K 2319/035; C07K 2319/61; C07K 14/195
See application file for complete search history.

(56) References Cited

U.S. PATENT DOCUMENTS

| | | | |
|---|---|---|---|
| 5,232,829 A * | 8/1993 | Longiaru | C12Q 1/6816 435/6.12 |
| 6,190,662 B1 | 2/2001 | Steidler et al. | |
| 9,394,534 B2 | 7/2016 | Beissinger et al. | |
| 2004/0197833 A1* | 10/2004 | Loessner | G01N 33/56911 435/7.2 |
| 2009/0136984 A1 | 5/2009 | Schultz et al. | |
| 2010/0092968 A1* | 4/2010 | Beissinger | C07K 14/005 435/320.1 |
| 2010/0317020 A1 | 12/2010 | Roscoe et al. | |
| 2018/0353575 A1* | 12/2018 | Fischetti | A61K 38/47 |

FOREIGN PATENT DOCUMENTS

| | | |
|---|---|---|
| CA | 2552284 A1 | 8/2005 |
| EP | 1356080 B1 | 8/2002 |
| WO | 2004072301 A1 | 8/2004 |
| WO | 2007022768 A2 | 3/2007 |
| WO | 2015109012 A1 | 7/2015 |

OTHER PUBLICATIONS

Lebonah et al., Advances in Biology, Article ID 541787, pp. 1-9, volume (Year: 2014).*
Kretzer, J.W., et al., "Use of High-Affinity Cell Wall-Binding Domains of Bacteriophage Endolysins for Immobilization and Separation of Bacterial Cells," Applied and Environmental Microbiology, vol. 73, No. 6, pp. 1992-2000, 2007.
Ahmed, A.B.F., et al., "Evaluation of Cell Wall Binding Domain of *Staphylococcus aureus* Autolysin as Affinity Reagent for Bacteria and Its Application to Bacterial Detection," Journal of Bioscience and Bioengineering, vol. 104, No. 1, pp. 55-61, 2007.
International Search Report and The Written Opinion of the International Searching Authority, International Application No. PCT/US2018/031511, dated Aug. 2, 2018.

* cited by examiner

*Primary Examiner* — Cynthia B Wilder
(74) *Attorney, Agent, or Firm* — Barclay Damon, LLC; Anthony P. Gangemi

(57) ABSTRACT

Methods and systems are directed to multiplex detection of a bacterial pathogen in a sample. A first biotinylated lysin-derived cell wall binding domain is complexed with an avidin layer on a surface. A first bacterial pathogen detection complex including a second biotinylated lysin-derived cell wall binding domain, a detection domain, and an avidin linker complexed between the cell wall binding domain and the detection domain is also provided. The cell wall binding domains are derived from an endolysin, autolysin, bacteriocin, or exolysin, and are configured to bind a cell wall of a target bacterial pathogen. The detection domain includes one or more enzymes, fluorescent material, or DNA for emitting a signal for detection. Target bacterial pathogens present in a sample can thus be detected in a sandwich assay exhibiting increased selectivity and reduced limit of detection relative to traditional ELISA.

12 Claims, 9 Drawing Sheets
Specification includes a Sequence Listing.

| Name | | Oligomer sequences | |
|---|---|---|---|
| BirA | Forward | 5'-AAGGAGATATACATATGAAGGATAACACCGTGCCACT-3' | (SEQ ID NO: 1) |
| | Reverse | 5'-TTGAGATCTGCCATATGTTATTTTCTGCACTACGCAGG-3' | (SEQ ID NO: 2) |
| Avi-EGFP | Forward | 5'-GCCAGGATCCGAATTCCATGTCAGGACTGAACGAT-3' | (SEQ ID NO: 3) |
| | Reverse | 5'-CGCCGAGCTCGAATTCCTTGTACAGCTCGTCCATGC-3' | (SEQ ID NO: 4) |
| CBD$^{SA}$ | Forward | 5'-GCGCCTGCAGGTCGACAAGGTTATGGCAAAGCCGGT-3' | (SEQ ID NO: 5) |
| | Reverse | 5'-CCGCAAGCTTGTCGACTTTGATGGTGCCCACAG-3' | (SEQ ID NO: 6) |
| CBD$^{BA}$ | Forward | 5'-GCGCCTGCAGGTCGACAAGGCGGTACCACGCCG-3' | (SEQ ID NO: 7) |
| | Reverse | 5'-CCGCAAGCTTGTCGACTTATTCACTTCATACCACCAACCA-3' | (SEQ ID NO: 8) |
| CBD$^{LI}$ | Forward | 5'-GCGCCTGCAGGTCGACTTATTACGAGGGTAAAGTCA-3' | (SEQ ID NO: 9) |
| | Reverse | 5'-CCGCAAGCTTGTGTCGACTTATTTTAAGAAGTATTCTGCTGTGTAAT-3' | (SEQ ID NO: 10) |

FIG. 4

|  | $CBD^{SA}$ | $CBD^{BA}$ | $CBD^{LI}$ |
|---|---|---|---|
| S. aureus | 0.92 | 0.08 | 0.06 |
| B. anthracis | 0.07 | 0.96 | 0.09 |
| L. innocua | 0.04 | 0.06 | 0.99 |
| S. aureus + B. anthracis | 0.96 | 0.93 | 0.04 |
| B. anthracis + L. innocua | 0.06 | 0.91 | 0.88 |
| S. aureus + L. innocua | 0.94 | 0.06 | 0.99 |
| S. aureus + B. anthracis + L. innocua | 1.00 | 1.00 | 1.00 |

FIG. 6

Biotin-DNA-barcode I
/5Biotin/CTGAATTCGCCCTTATGGCTCTCATCCAGACTTGGCCATGG (SEQ ID NO: 11)
AAACCTGGCTCTCTGGCTGTCAGCCTGGTGCTCCTATCTATATGG
AACCCATTCACATGGACTTTTAAGAAGGAATTCAG

Biotin-DNA-barcode II
/5Biotin/CTGAATTCCCAGTCCGCCCTGAGCAAAGACCCCAACGAGA (SEQ ID NO: 12)
AGCGCGATCACATGGTCCTGGAGTTCGTGACGCCGCGGGATC
ACTCTCGGCATGGACGAGCTGTACAAGTAA

Biotin-DNA-barcode III
/5Biotin/CTGAATTCGCTATGAAAGCAGAAGGGTTTAAATGGGGCGG (SEQ ID NO: 13)
AGACTGGAAAAGTTTAAAGACTATCCGCATTTGAACTATGTGATGCT
GTAAGTGGTGAGAAAATCCCTGCAACAAAACACTAATACAAAT
TCAAATCGTTACGAGGGTAAAGTCATTGATAGCGC

FIG. 7

| Name | | Oligomer sequences | |
|---|---|---|---|
| DNA-barcode-I | Forward | /5'-Biosg/CTGAATTCGCCCTTATGGCTC-3' | (SEQ ID NO: 14) |
| | Reverse | 5'-CTGAATTCCTTCTTAAAAGTCCATGTGAATG-3' | (SEQ ID NO: 15) |
| DNA-barcode-II | Forward | /5'-Biosg/CTGAATTCCCAGTCCGCCCTGAG-3' | (SEQ ID NO: 16) |
| | Reverse | 5'-TTACTTGTACAGTCGTCC-3' | (SEQ ID NO: 17) |
| DNA-barcode-III | Forward | /5'-Biosg/CTGAATTCGCTATGAAAGCAGAAGG-3' | (SEQ ID NO: 18) |
| | Reverse | 5'-GCGCTATCAATGACTTTAC-3' | (SEQ ID NO: 19) |
| qPCR of DNA-barcode-I | Forward | 5'-ATGGCTCTCATCCCAGACTT-3' | (SEQ ID NO: 20) |
| | Reverse | 5'-AGTCCATGTGAATGGGTTCC-3' | (SEQ ID NO: 21) |
| qPCR of DNA-barcode-II | Forward | 5'-GAAGCGGATCACATGGT-3' | (SEQ ID NO: 22) |
| | Reverse | 5'-CCATGCCGAGAGTGATCC-3' | (SEQ ID NO: 23) |
| qPCR of DNA-barcode-III | Forward | 5'-GGAGACTGGAAAAGTTTTAAAG-3' | (SEQ ID NO: 24) |
| | Reverse | 5'-GAATTTGTATTAGTGTTTTGTGTTG-3' | (SEQ ID NO: 25) |

SEQUENCE LISTING

<160> NUMBER OF SEQ ID NOS: 25

<210> SEQ ID NO 1
<211> LENGTH: 37
<212> TYPE: DNA
<213> ORGANISM: Artificial Sequence
<220> FEATURE:
<223> OTHER INFORMATION: Synthetic oligomer sequence

<400> SEQUENCE: 1
aaggagatat acatatgaag gataacaccg tgccact                37

<210> SEQ ID NO 2
<211> LENGTH: 39
<212> TYPE: DNA
<213> ORGANISM: Artificial Sequence
<220> FEATURE:
<223> OTHER INFORMATION: Synthetic oligomer sequence

<400> SEQUENCE: 2
ttgagatctg ccatatgtta tttttctgca ctacgcagg             39

<210> SEQ ID NO 3
<211> LENGTH: 35
<212> TYPE: DNA
<213> ORGANISM: Artificial Sequence
<220> FEATURE:
<223> OTHER INFORMATION: Synthetic oligomer sequence

<400> SEQUENCE: 3
gccaggatcc gaattccatg tcaggactga acgat                 35

<210> SEQ ID NO 4
<211> LENGTH: 36
<212> TYPE: DNA
<213> ORGANISM: Artificial Sequence
<220> FEATURE:
<223> OTHER INFORMATION: Synthetic oligomer sequence

<400> SEQUENCE: 4
cgccgagctc gaattccttg tacagctcgt ccatgc                36

<210> SEQ ID NO 5
<211> LENGTH: 36
<212> TYPE: DNA
<213> ORGANISM: Artificial Sequence
<220> FEATURE:
<223> OTHER INFORMATION: Synthetic oligomer sequence

<400> SEQUENCE: 5
gcgcctgcag gtcgacaagg ttatggcaaa gccggt                36

<210> SEQ ID NO 6
<211> LENGTH: 34
<212> TYPE: DNA
<213> ORGANISM: Artificial Sequence
<220> FEATURE:
<223> OTHER INFORMATION: Synthetic oligomer sequence

<400> SEQUENCE: 6
ccgcaagctt gtcgactttg atggtgcccc acag                  34

<210> SEQ ID NO 7
<211> LENGTH: 33
<212> TYPE: DNA
<213> ORGANISM: Artificial Sequence
<220> FEATURE:
<223> OTHER INFORMATION: Synthetic oligomer sequence

<400> SEQUENCE: 7
gcgcctgcag gtcgacaagg cggtaccacg ccg                   33

<210> SEQ ID NO 8
<211> LENGTH: 41
<212> TYPE: DNA
<213> ORGANISM: Artificial Sequence
<220> FEATURE:
<223> OTHER INFORMATION: Synthetic oligomer sequence

<400> SEQUENCE: 8
ccgcaagctt gtcgacttat ttcacttcat accaccaacc a        41

<210> SEQ ID NO 9
<211> LENGTH: 41
<212> TYPE: DNA
<213> ORGANISM: Artificial Sequence
<220> FEATURE:
<223> OTHER INFORMATION: Synthetic oligomer sequence

<400> SEQUENCE: 9
gcgcctgcag gtcgacaaaa atcgttacga gggtaaagtc a        41

<210> SEQ ID NO 10
<211> LENGTH: 45
<212> TYPE: DNA
<213> ORGANISM: Artificial Sequence
<220> FEATURE:
<223> OTHER INFORMATION: Synthetic oligomer sequence

<400> SEQUENCE: 10
ccgcaagctt gtcgacttat tttaagaagt attctgctgt gtaat    45

<210> SEQ ID NO 11
<211> LENGTH: 127
<212> TYPE: DNA
<213> ORGANISM: Artificial Sequence
<220> FEATURE:
<223> OTHER INFORMATION: Sythetic DNA sequence

<400> SEQUENCE: 11
ctgaattcgc ccttatggct ctcatcccag acttggccat ggaaacctgg cttctcctgg    60
ctgtcagcct ggtgctcctc tatctatatg gaacccattc acatggactt tttaagaagg   120
aattcag                                                             127

<210> SEQ ID NO 12
<211> LENGTH: 117
<212> TYPE: DNA
<213> ORGANISM: Artificial Sequence
<220> FEATURE:
<223> OTHER INFORMATION: Synthetic DNA sequence

<400> SEQUENCE: 12
ctgaattccc agtccgccct gagcaaagac cccaacgaga agcgcgatca catggtcctg    60
ctggagttcg tgaccgccgc cgggatcact ctcggcatgg acgagctgta caagtaa     117

<210> SEQ ID NO 13
<211> LENGTH: 172
<212> TYPE: DNA
<213> ORGANISM: Artificial Sequence
<220> FEATURE:
<223> OTHER INFORMATION: Synthetic DNA sequence

<400> SEQUENCE: 13
ctgaattcgc tatgaaagca gaagggttta atggggcgg agactggaaa agttttaaag    60
actatccgca ttttgaacta tgtgatgctg taagtggtga gaaaatccct gctgcaacac   120
aaaacactaa tacaaattca aatcgttacg agggtaaagt cattgatagc gc        172

<210> SEQ ID NO 14
<211> LENGTH: 21
<212> TYPE: DNA
<213> ORGANISM: Artificial Sequence
<220> FEATURE:
<223> OTHER INFORMATION: Synthetic oligomer sequence

<400> SEQUENCE: 14
ctgaattcgc ccttatggct c        21

<210> SEQ ID NO 15
<211> LENGTH: 32
<212> TYPE: DNA
<213> ORGANISM: Artificial Sequence
<220> FEATURE:
<223> OTHER INFORMATION: Synthetic oligomer sequence

<400> SEQUENCE: 15
ctgaattcct tcttaaaaag tccatgtgaa tg        32

<210> SEQ ID NO 16
<211> LENGTH: 23
<212> TYPE: DNA
<213> ORGANISM: Artificial Sequence
<220> FEATURE:
<223> OTHER INFORMATION: Synthetic oligomer sequence

<400> SEQUENCE: 16
ctgaattccc agtccgccct gag        23

<210> SEQ ID NO 17
<211> LENGTH: 19
<212> TYPE: DNA
<213> ORGANISM: Artificial Sequence
<220> FEATURE:
<223> OTHER INFORMATION: Synthetic oligomer sequence

<400> SEQUENCE: 17
ttacttgtac agctcgtcc        19

<210> SEQ ID NO 18
<211> LENGTH: 25
<212> TYPE: DNA
<213> ORGANISM: Artificial Sequence
<220> FEATURE:
<223> OTHER INFORMATION: Synthetic oligomer sequence

<400> SEQUENCE: 18
ctgaattcgc tatgaaagca gaagg        25

<210> SEQ ID NO 19
<211> LENGTH: 19
<212> TYPE: DNA
<213> ORGANISM: Artificial Sequence
<220> FEATURE:
<223> OTHER INFORMATION: Synthetic oligomer sequence

<400> SEQUENCE: 19
gcgctatcaa tgactttac        19

<210> SEQ ID NO 20
<211> LENGTH: 20
<212> TYPE: DNA

-continued

```
<213> ORGANISM: Artificial Sequence
<220> FEATURE:
<223> OTHER INFORMATION: Synthetic oligomer sequence

<400> SEQUENCE: 20
atggctctca tcccagactt                                                    20

<210> SEQ ID NO 21
<211> LENGTH: 20
<212> TYPE: DNA
<213> ORGANISM: Artificial Sequence
<220> FEATURE:
<223> OTHER INFORMATION: Synthetic oligomer sequence

<400> SEQUENCE: 21
agtccatgtg aatgggttcc                                                    20

<210> SEQ ID NO 22
<211> LENGTH: 18
<212> TYPE: DNA
<213> ORGANISM: Artificial Sequence
<220> FEATURE:
<223> OTHER INFORMATION: Synthetic oligomer sequence

<400> SEQUENCE: 22
gaagcgcgat cacatggt                                                      18

<210> SEQ ID NO 23
<211> LENGTH: 18
<212> TYPE: DNA
<213> ORGANISM: Artificial Sequence
<220> FEATURE:
<223> OTHER INFORMATION: Synthetic oligomer sequence

<400> SEQUENCE: 23
ccatgccgag agtgatcc                                                      18

<210> SEQ ID NO 24
<211> LENGTH: 22
<212> TYPE: DNA
<213> ORGANISM: Artificial Sequence
<220> FEATURE:
<223> OTHER INFORMATION: Synthetic oligomer sequence

<400> SEQUENCE: 24
ggagactgga aaagttttaa ag                                                 22

<210> SEQ ID NO 25
<211> LENGTH: 25
<212> TYPE: DNA
<213> ORGANISM: Artificial Sequence
<220> FEATURE:
<223> OTHER INFORMATION: Synthetic oligomer sequence

<400> SEQUENCE: 25
gaatttgtat tagtgttttg tgttg                                              25
```

MULTIPLEX DETECTION OF BACTERIAL PATHOGENS VIA CELL WALL BINDING DOMAIN COMPLEXES

CROSS REFERENCE TO RELATED APPLICATION(S)

This application is a national stage patent filing of International Patent Application No. PCT/US2018/031511, filed May 8, 2018, which claims the benefit of U.S. Provisional Application Nos. 62/502,856, filed May 8, 2017, 62/647,292, filed Mar. 23, 2018, and 62/667,998, filed May 7, 2018, which are incorporated by reference as if disclosed herein in their entirety.

BACKGROUND

Enzyme-linked immunosorbent assays (ELISA) are a well-known and powerful diagnostic technique for detecting and quantifying a broad range of targets. Traditional ELISA often relies on specifically designed antibodies for capturing and detecting these targets. However, even the most thoughtfully designed antibody suffers from issues with limits of detection (LOD), particularly when the target is a bacterial pathogen. Conserved epitopes across related and unrelated species risk false positives or high levels of non-specific binding, and thus can be of limited use depending on the source to be tested. These specifically designed antibodies are also expensive and laborious to create.

In an attempt to overcome these and other drawbacks associated with traditional ELISA protocols, alternative methods have been employed, particularly when bacterial pathogens are the target. For example, polymerase chain reaction (PCR) has been used to target bacteria utilizing species-specific primers. However, due to the high sensitivity of PCR and the presence of contaminants, this technique is prone to both false positive and false negative results, rendering it generally unsuitable for widespread use in bacterial pathogen detection, such as in food or non-laboratory medical testing.

SUMMARY

Some embodiments of the disclosed subject matter are directed to a bacterial pathogen detection complex including a lysin-derived cell wall binding domain, a detection domain configured to produce a signal for detection, and a linker complexed between the cell wall binding domain and the detection domain. In some embodiments, the lysin-derived cell wall binding domain is derived from a cell wall binding domain from an endolysin, autolysin, bacteriocin, or exolysin, and is configured to bind a cell wall of a target bacterial pathogen. In some embodiments, the lysin-derived cell wall binding domain is configured to selectively bind to members of the genus *Staphylococcus, Bacillus, Listeria, Streptococcus, Lactobacillus, Mycobacterium, Enterococcus, Pneumococcus, Salmonella, Campylobacter, Escherichia, Vibrio, Shigella, Pseudomonas,* or *Clostridia*. In some embodiments, the lysin-derived cell wall binding domain is derived from lysostaphin, SA1, AmiBA2446, Ply500, Cpl-1, CD11, CDG, plyG, PlyC, CD27L, LysA, gp36, gp16, gp3, HydH5, CwlT, At1L, enerolysin A, Helviticin J, Millericin B, or mutanolysin. In some embodiments, the signal for detection is enzymatic activity of the detection domain, fluorescent signal, a light signal, a radiofrequency signal, electrochemical signal, or combinations thereof. In some embodiments, the detection domain includes an enzyme, fluorescent material, or DNA. In some embodiments, the enzyme is a glucose oxidase ($GO_x$), galactose oxidase, alcohol oxidase, cholesterol oxidase, peroxidase, α- or β-galactosidase, α- or β-glucosidase, α- or β-amylase, alkaline phosphatase, luciferase, or cellulase, and others with suitable chromogenic or fluorogenic substrates. In some embodiments, the enzymes are coupled to a peroxidase for detection using chromogenic or fluorogenic substrates. In some embodiments, multiple enzymes can be used to generate the detection signal. In some embodiments, the fluorescent materials include fluorescent chemicals, fluorescent nanoparticles/beads, fluorescent proteins such as blue fluorescent protein (BFP), cyan fluorescent protein (CFP), yellow fluorescent protein (YFP), green fluorescent protein (GFP), red fluorescent protein (RFP), etc., or combinations thereof. In some embodiments, the DNA includes a DNA amplicon and is configured for use in a polymerase chain reaction process. In some embodiments, at least one of the lysin-derived cell wall binding domain and the detection domain are biotinylated. In some embodiments, the linker is an avidin linker. In some embodiments, the avidin linker is an avidin, streptavidin, neutravidin, or captavidin.

Some embodiments of the disclosed subject matter are directed to a bacterial pathogen detection kit including a surface including an avidin layer, a first biotinylated lysin-derived cell wall binding domain complexed with the avidin layer to substantially immobilize the first biotinylated lysin-derived cell wall binding domain with respect to the surface, and a first bacterial pathogen detection complex. In some embodiments, the first bacterial pathogen detection complex includes a second biotinylated lysin-derived cell wall binding domain, a detection domain, and an avidin linker complexed between the cell wall binding domain and the detection domain. In some embodiments, the first and second lysin-derived cell wall binding domains are derived from a cell wall binding domain from an endolysin, autolysin, bacteriocin, or exolysin, and are configured to bind a cell wall of a first target bacterial pathogen. In some embodiments, the first and second lysin-derived cell wall binding domains are configured to selectively bind to members of the genus *Staphylococcus, Bacillus, Listeria, Streptococcus, Lactobacillus, Mycobacterium, Enterococcus, Pneumococcus, Salmonella, Campylobacter, Escherichia, Vibrio, Shigella, Pseudomonas,* or *Clostridia*. In some embodiments, the first and second lysin-derived cell wall binding domains are derived from lysostaphin, SA1, AmiBA2446, Ply500, Cpl-1, CD11, CDG, plyG, PlyC, CD27L, LysA, gp36, gp16, gp3, HydH5, CwlT, At1L, enerolysin A, Helviticin J, Millericin B, or mutanolysin. In some embodiments, the kit includes a third biotinylated lysin-derived cell wall binding domain complexed with the avidin layer and a second bacterial pathogen detection complex including a fourth biotinylated lysin-derived cell wall binding domain, wherein the third and fourth biotinylated lysin-derived cell wall binding domain are configured to bind a cell wall of a second target bacterial pathogen.

Some embodiments of the disclosed subject matter are directed to a method of detecting a bacterial pathogen including providing an avidin layer on a surface. In some embodiments, the method includes complexing a first biotinylated lysin-derived cell wall binding domain with the avidin layer. In some embodiments, the method includes applying a sample to be tested for a target bacterial pathogen to the surface. In some embodiments, the method includes applying a bacterial pathogen detection complex to the sample. In some embodiments, the method includes detecting a signal produced from the surface by the detection domain as an indicator that a bacterial pathogen is bound to the first and second biotinylated lysin-derived cell wall binding domain. In some embodiments, detecting the signal produced from the surface by the detection domain includes a real-time polymerase chain reaction process, an enzymatic activity assay, or combinations thereof.

BRIEF DESCRIPTION OF THE DRAWINGS

The drawings show embodiments of the disclosed subject matter for the purpose of illustrating the invention. However, it should be understood that the present application is not limited to the precise arrangements and instrumentalities shown in the drawings, wherein:

FIG. 4 portrays a list of primers used to construct pHis-Avi-EGFP-CBD-BirA according to some embodiments of the disclosed subject matter;

FIG. 6 portrays normalized signal-to-noise ratio from various bacterial mixtures;

FIG. 7 portray DNA sequences coding the DNA barcodes according to some embodiments of the disclosed subject matter;

FIG. 8 portray a list of primers for the synthesis of 5'-biotinylated DNA-barcodes and the real-time polymerase chain reaction (qPCR) amplification of DNA amplicons according to some embodiments of the disclosed subject matter.

DETAILED DESCRIPTION

Figure 1:
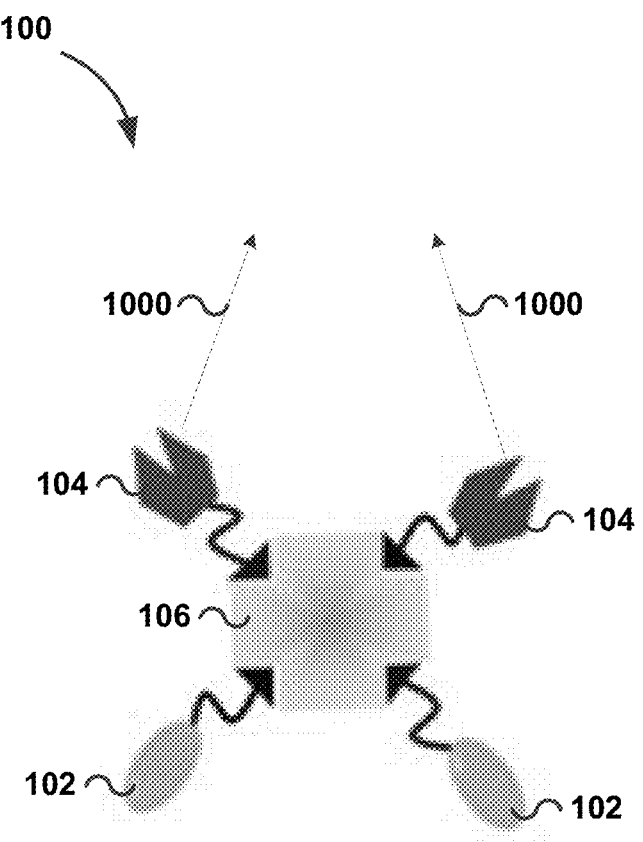
FIG. 1 is a schematic drawing of a bacterial pathogen detection complex according to some embodiments of the disclosed subject matter.

Referring now to FIG. 1, aspects of the disclosed subject matter include a bacterial pathogen detection complex 100 including at least one cell wall binding domain 102. Cell wall binding domain 102 is configured to bind to the cell walls of a target bacterial pathogen. In some embodiments, the cell wall binding domain 102 is a cell wall binding domain (CBD) from a lysin, e.g., from an endolysin, autolysin, bacteriocin, or exolysin. In some embodiments, the cell wall binding domain 102 is configured to selectively bind to members of the genus *Staphylococcus, Bacillus, Listeria, Streptococcus, Lactobacillus, Mycobacterium, Enterococcus, Pneumococcus, Salmonella, Campylobacter, Escherichia, Vibrio, Shigella, Pseudomonas,* or *Clostridia*. Without wishing to be bound by theory, any bacterium susceptible to a lysin selective to that bacterium would be a target bacterium according to an embodiment of the present disclosure. In some embodiments, the cell wall binding domain 102 is configured to selectively bind to a specific species of bacterial pathogen from these genera. Without wishing to be bound by theory, a typical bacterial pathogen can have more than $10^7$ binding sites present on their cell walls, to which the CBDs of lysins have a binding affinity comparable to that of an antibody for its antigen. Further, lysin CBDs tend to selectively target specific bacteria, meaning the cell wall binding domain 102 will bind strongly with target bacterial pathogens in a sample with minimal non-selective binding to other substrates or non-target bacterial pathogens. In some embodiments, the cell wall binding domain 102 is from lysostaphin, SA1, AmiBA2446, Ply500, Cpl-1, CD11, CDG, plyG, PlyC, CD27L, LysA, gp36, gp16, gp3, HydH5, CwlT, AtlL, enerolysin A, Helviticin J, Millericin B, or mutanolysin. A non-limiting list of lysins suitable for use as the source of the cell wall binding domains as shown and described in the present disclosure is included at Table 1 below.

TABLE 1

List of lysins suitable for use as the CBD source

| Enzyme | Category | Origin | Target bacteria | Activity | Domain |
|--------|----------|--------|-----------------|----------|--------|
| PlyG | Endolysin | γ phage | *Bacillus anthracis* *Bacillus cereus* | Amidase | N: catalytic C: binding |
| PlyC | Endolysin | C1 phage | Streptococci | Peptidase Glycosidase | N: catalytic C: binding |
| Cpl-1 | Endolysin | *Streptococcus* phage Cp-1 | *Streptococcus pneumoniae* | Muramidase | N: catalytic C: binding |
| Ply500 | Endolysin | ΦA500 | *Listeria monocytogenes* | Peptidase | N: catalytic C: binding |
| CD27L | Endolysin | ΦCD27 | *Clostridium difficile* | Amidase | N: catalytic C: binding |
| LysA | Endolysin | ΦMs6 | *Mycobacterium tuberculosis* | Amidase | N: catalytic C: binding |
| gp36 | VAL | ΦKMV | *Pseudomonas aeruginosa* | Muramidase | C: catalytic |
| gp16 | VAL | ΦT7 | *Escherichia coli* | | |
| gp3 | VAL | Φ29 | *B. subtilis* | | |
| HydH5 | VAL | vB_SauS-phiIPLA88 | *Staphylococcus aureus* | Amidase Muramidase | N: CHAP C: LYZ2 |
| LysA | Autolysin | *Lactobacillus fermentum* | *L. fermentum* | Muramidase like | N: catalytic C: binding |
| CwlT | Autolysin | *Bacillus subtilis* | *B. subtilis* | Muramidase/ endopeptidase | N: catalytic C: catalytic |

TABLE 1-continued

List of lysins suitable for use as the CBD source

| Enzyme | Category | Origin | Target bacteria | Activity | Domain |
|---|---|---|---|---|---|
| AtlL | Autolysin | Staphylococcus lugdunensis | S. lugdunensis | Amidase, glucose-aminidase | N: catalytic C: catalytic |
| AmiBA2446 | Autolysin | B. anthracis | B. cereus B. anthracis | Amidase | N: catalytic C: binding |
| CD11 CDG | Autolysin | C. difficile | C. difficile | Amidase | N: catalytic C: binding |
| Lysostaphin | Bacteriocin | Staphylococcus simulans | S. aureus | Endopeptidase | N: catalytic C: binding |
| SA1 | Autolysin | Staphylococcus aureus | S. aureus | N-acetylmuramoyl-L-alanine amidase | N: catalytic C: binding |
| enterolysin A | Bacteriocin | Enterococcus faecalis | Enterococcus faecium Lactococcus lactis Listeria innocua | | |
| Helviticin J | Bacteriocin | Lactobacillus helveticus | L. helveticus L. lactis Lactobacillus delbrueckii subsp. bulgaricus | | |
| Millericin B | Bacteriocin | Streptococcus milleri | Gram-positive | Endopeptidase | |
| Mutanolysin | Bacteriocin | Streptomyces globisporus | Streptococcus mutans | Muramidase | N: catalytic C: binding |

While the cell wall binding domain 102 is described in the present disclosure as that as found in a lysin, the cell wall binding domain 102 is not limited in this regard. One of ordinary skill in the art would understand that cell wall binding domain 102 could also be a functional equivalent of a wild-type cell wall binding domain, e.g., including one or more mutations, additions, truncations, etc., while retaining the functionality of the wild-type cell wall binding domain. As used herein, the term "lysin-derived" when referring to a CBD is used to refer to wild-type cell wall binding domains, as well as domains derived from wild-type cell wall binding domains that do not substantially differ in their ability, relative to the wild-type, to bind the cell wall of a bacterial pathogen, e.g., include one or more mutations, additions, truncations, etc., while retaining the functionality of the wild-type cell wall binding domain.

Still referring to FIG. 1, bacterial pathogen detection complex 100 includes at least one detection domain 104. Detection domain 104 is configured to produce a signal 1000. The signal 1000 is any signal suitable for detection, e.g., enzymatic activity of the detection domain, a fluorescent signal, a light signal (e.g., ultraviolet, visible and infrared signal), a radiofrequency signal, electrochemical signal, etc., or combinations thereof. In some embodiments, the detection domain 104 is one or more proteins, one or more fluorescent materials, DNA, or combinations thereof. In some embodiments, the one or more proteins include one or more enzymes with a measurable activity, e.g., glucose oxidase ($GO_x$), galactose oxidase, alcohol oxidase, cholesterol oxidase, peroxidase, α- or β-galactosidase, α- or β-glucosidase, α- or β-amylase, alkaline phosphatase, luciferase, or cellulase, and others with suitable chromogenic or fluorogenic substrates. In some embodiments, the enzymes are be coupled to a peroxidase for detection using chromogenic or fluorogenic substrates. In some embodiments, the fluorescent materials include fluorescent chemicals, fluorescent nanoparticles/beads, fluorescent proteins such as BFP, CFP, YFP, GFP, RFP, etc., or combinations thereof. In some embodiments, the DNA includes one or more DNA amplicons. In some embodiments, the DNA amplicons form a DNA barcode specific to a target bacterial pathogen. The DNA can be any suitable configuration or construction so long as the presence and/or quantity of DNA can be detected in an assay, e.g., via PCR, qPCR, etc., as will be discussed in greater detail below.

In some embodiments, the cell wall binding domain 102 and the detection domain 104 are complexed together. In some embodiments, the cell wall binding domain 102 and the detection domain 104 are complexed with a linker 106. In some embodiments, the linker 106 is disposed between the cell wall binding domain 102 and the detection domain 104.

In some embodiments, at least one of the cell wall binding domain 102 and the detection domain 104 is biotinylated. In some of these embodiments, the linker 106 is an avidin linker, e.g., avidin, streptavidin, neutravidin, captavidin, etc.

Figure 2A:
FIG. 2A is a schematic drawing of a cell wall binding domain according to some embodiments of the disclosed subject matter.

Referring now to FIG. 2A, aspects of the disclosed subject matter include a separate additional cell wall binding domain 202. Cell wall binding domain 202 is configured to bind to the cell walls of a target bacterial pathogen. As with cell wall binding domain 102, in some embodiments, cell wall binding domain 202 is a cell wall binding domain from a lysin, e.g., from an endolysin, autolysin, bacteriocin, or exolysin. In some embodiments, the lysin-derived cell wall binding domain is configured to selectively bind to members of the genus Staphylococcus, Bacillus, Listeria, Streptococcus, Lactobacillus, Mycobacterium, Enterococcus, Pneumococcus, Salmonella, Campylobacter, Escherichia, Vibrio, Shigella, Pseudomonas, or Clostridia. In some embodiments, the cell wall binding domain 102 is configured to selectively bind to a specific species of bacterial pathogen from these genera. As discussed above, lysin CBDs tend to selectively target specific bacteria, meaning the cell wall binding domain 202 will bind strongly with target bacterial pathogens in a sample with minimal non-selective binding to other substrates or non-target bacterial pathogens. In some embodiments, the cell wall binding domain 202 is derived from lysostaphin, SA1, AmiBA2446, Ply500, Cpl-1, CD11, CDG, plyG, PlyC, CD27L, LysA, gp36, gp16, gp3, HydH5, CwlT, Atl1L, enerolysin A, Helviticin J, Millericin B, or mutanolysin.

While the cell wall binding domain 202 is described in the present disclosure as that found in a lysin, the cell wall binding domain 202 is not limited in this regard. One of ordinary skill in the art would understand that cell wall binding domain 202 could also be derived from a wild-type cell wall binding domain, e.g., including one or more mutations, additions, truncations, etc., and retain the functionality of the wild-type cell wall binding domain. As used herein, the cell wall binding domain 202 includes wild-type cell wall binding domains, as well as domains derived from wild-type cell wall binding domains that do not substantially differ in their ability, relative to the wild-type, to bind the cell wall of a bacterial pathogen, e.g., include one or more mutations, additions, truncations, etc., while retaining the functionality of the wild-type cell wall binding domain.

In some embodiments, cell wall binding domain 102 and cell wall binding domain 202 have the same structure. In some embodiments, cell wall binding domain 102 and cell wall binding domain 202 have different structures. In some embodiments, cell wall binding domain 102 and cell wall binding domain 202 are configured to bind the same target bacterial pathogen.

In some embodiments, cell wall binding domain 202 are configured to attach to a surface, e.g., a well plate, a bead, a dipstick, a paddle, a pipette, other solid matrix, etc. The surface is configured so that the cell ball binding domain 202 is complexed to the surface, yet remains free to bind target bacterial pathogens. In some embodiments, the cell wall binding domain 202 is biotinylated. In some embodiments, the surface is at least partially coated with an avidin layer, e.g., avidin, streptavidin, neutravidin, captavidin, etc. The biotinylated cell wall binding domain 202 are complexed via the interactions between the biotin and the avidin on the surface. As will be discussed in greater detail below, by complexing the cell wall binding domain 202 on the surface, a sample suspected of including a target bacterial pathogen can be provided to the surface and through binding with cell wall binding domain 202, target bacterial pathogens can be substantially immobilized on the surface as well.

Figure 2B:
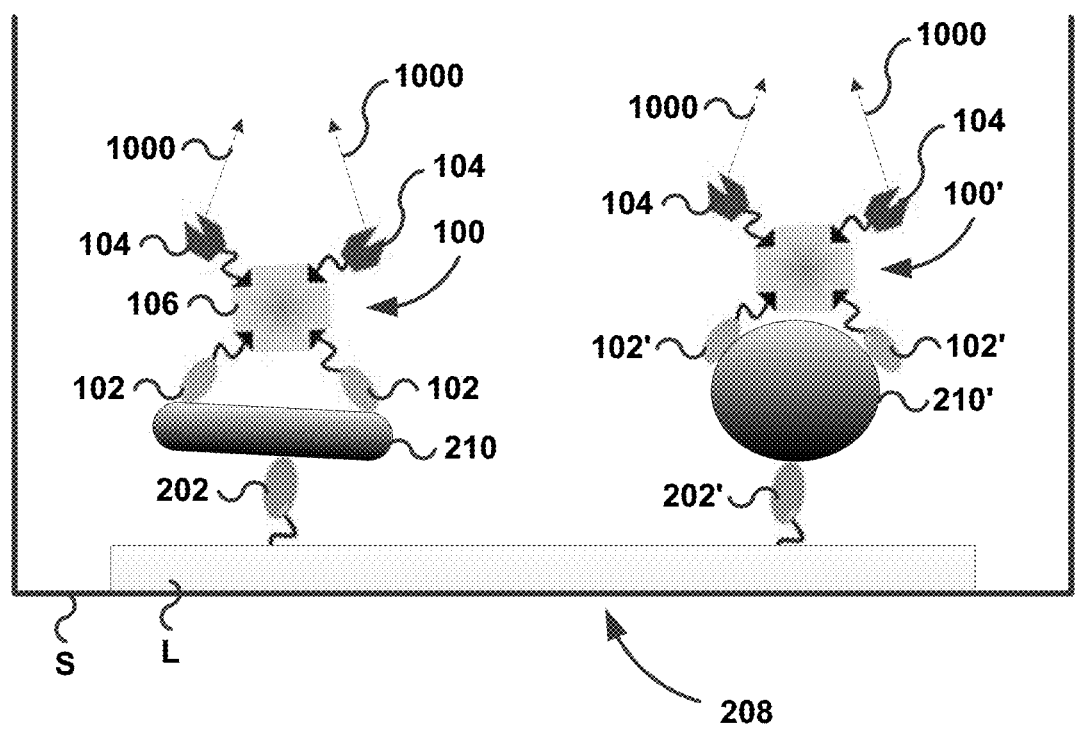
FIG. 2B is a schematic drawing of a bacterial pathogen detection kit according to some embodiments of the disclosed subject matter.

Referring now to FIG. 2B, in some embodiments, bacterial pathogen detection complex 100 and cell wall binding domain 202 are provided as a kit 208 for detecting a target bacterial pathogen 210. In some embodiments, the kit 208 includes a surface S. As discussed above, in some embodiments, surface S includes a layer L disposed at least partially thereon. One or both of surface S and layer L is configured to complex with cell wall binding domain 202 and substantially immobilize it with respect to the surface S, while the cell wall binding domain 202 remains free to bind with target bacterial pathogen 210. In some embodiments, the cell wall binding domain 202 is reversibly complexed with one or both of surface S and layer L. In some embodiments, the cell wall binding domain 202 is irreversibly complexed with one or both of surface S and layer L. In some embodiments, the cell wall binding domain 202 is biotinylated and layer L includes an avidin linker, e.g., avidin, streptavidin, neutravidin, captavidin, etc.

Kit 208 also includes the bacterial pathogen detection complex 100. As discussed above, bacterial pathogen detection complex 100 includes a cell wall binding domain 102. Both cell wall binding domain 102 and cell wall binding domain 202 are configured to bind to the same target bacterial pathogen 210, e.g., in a "sandwich" configuration with the target bacterial pathogen 210 disposed between cell wall binding domain 102 and cell wall binding domain 202. In some embodiments, the binding of cell wall binding domain 102 and cell wall binding domain 202 is reversible. In some embodiments, the binding of cell wall binding domain 102 and cell wall binding domain 202 is irreversible. In some embodiments, cell wall binding domain 102 and cell wall binding domain 202 are each derived from the same lysin. In some embodiments, cell wall binding domain 102 and cell wall binding domain 202 are derived from different lysins. Also as discussed above, the bacterial pathogen detection complex 100 includes detection domain 104, e.g., one or more proteins or DNA, complexed with cell wall binding domain 102, e.g., biotinylated and linked via avidin, streptavidin, neutravidin, or captavidin. Detection domain 104 is configured to produce the signal 1000. Thus, when a sample is applied to kit 208, target bacterial pathogens 210 included in that sample are substantially immobilized on surface S by binding with cell wall binding domain 102. Bacterial pathogen detection complex 100 is then bound to the substantially immobilized target bacterial pathogens 210 via cell wall binding domain 202. Thus bound, signal 1000 can be detected from detection domain 104 to indicate a presence or amount of target bacterial pathogen 210 in the sample. As the binding of cell wall binding domain 202 with target bacterial pathogen 210 is highly specific, unbound bacterial pathogen detection complexes, e.g., those for other targets, are easily removed from the environment surrounding the cell wall binding domain 202-target bacterial pathogen 210 complexes. The detection of signal 1000 is thus substantially limited to bound CBDs, which also limits false positives and lowers LOD.

In some embodiments, additional pairs of bacterial pathogen detection complex 100 and cell wall binding domain 202, e.g., a third cell wall binding domain 202' and a second bacterial pathogen detection complex 100' (including a fourth cell wall binding domain 102'), are provided to detect additional target bacterial pathogens 210' in a multiplex detection scheme. Additional pairs can be provided as needed to test a sample for each additional target bacterial pathogen. In some embodiments, the cell wall binding domains of bacterial pathogen detection complex 100 and bacterial pathogen detection complex 100' are configured to bind the same bacterial pathogen. In some embodiments, the cell wall binding domains of bacterial pathogen detection complex 100 and bacterial pathogen detection complex 100' are configured to bind different bacterial pathogens. In some embodiments, the second bacterial pathogen detection complex 100' has a different cell wall binding domain but the same detection domain compared to bacterial pathogen detection complex 100. In some embodiments, the second bacterial pathogen detection complex 100' has the same cell wall binding domain but different detection domain compared to bacterial pathogen detection complex 100. In these embodiments, the detection of bacterial pathogens 210 can be based on the combination of multiple, e.g., two or more, detection domains.

Figure 3:
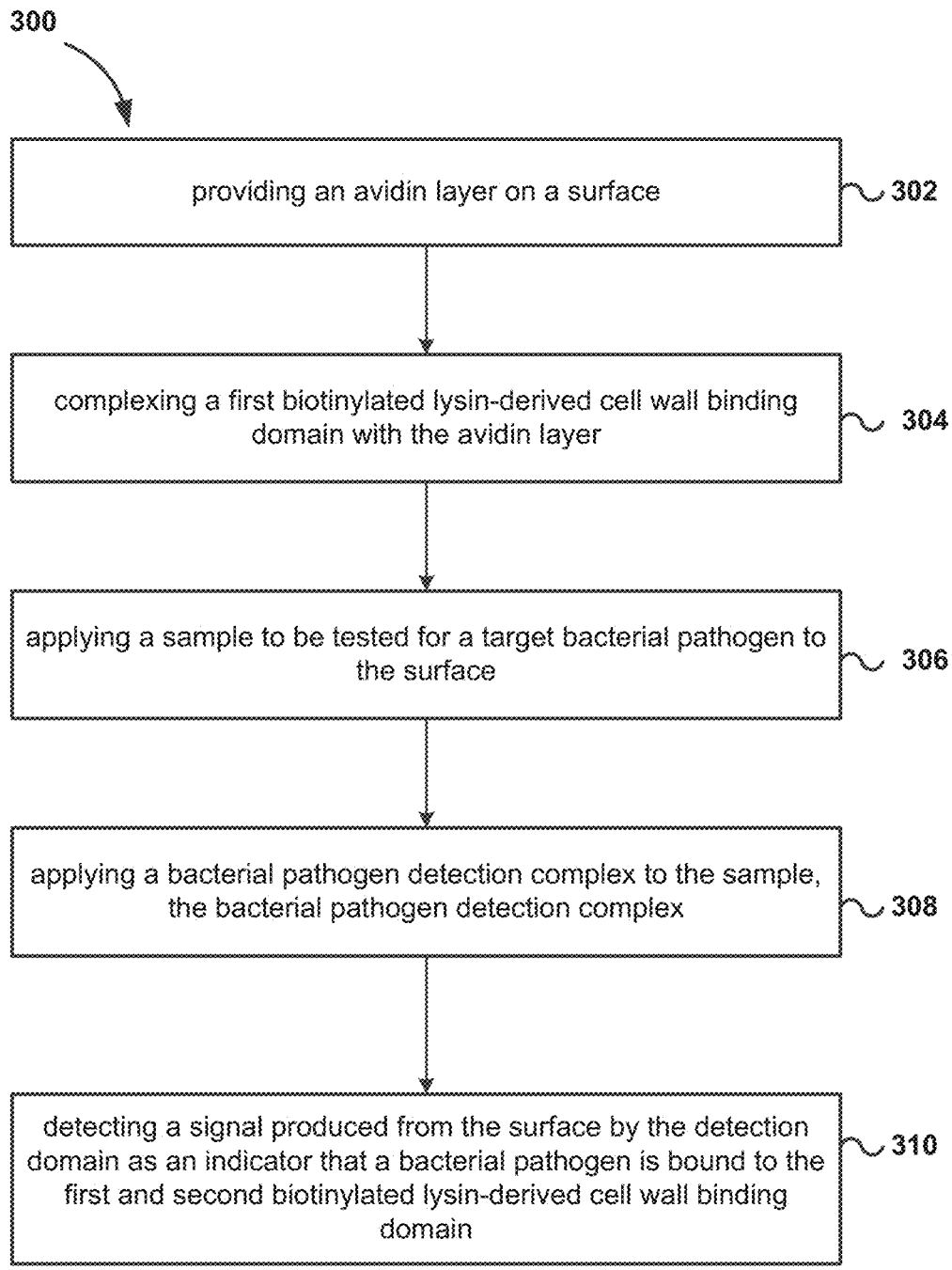
FIG. 3 is a chart of a method of detecting a bacterial pathogen according to some embodiments of the disclosed subject matter.

Referring now to FIG. 3, aspects of the disclosed subject matter include a method 300 of detecting a bacterial pathogen. At 302, an avidin layer is provided to a surface. At 304, a first biotinylated lysin-derived cell wall binding domain is complexed with the avidin layer. At 306, a sample to be tested for a target bacterial pathogen is applied to the surface. At 308, a bacterial pathogen detection complex is applied to the sample. As discussed above, in some embodiments, the bacterial pathogen detection complex includes a second biotinylated lysin-derived cell wall binding domain, a detection domain, and an avidin linker complexed between the cell wall binding domain and the detection domain. At 310, a signal produced from the surface by the detection domain is detected as an indicator that a bacterial pathogen is bound to the first and second biotinylated lysin-derived cell wall binding domain. The method 300 is effective as a linked cell wall binding domain sorbent assay capable of detecting multiple bacterial pathogens with a single sample. As discussed above, detecting the signal produced from the surface by the detection domain includes a PCR process, a qPCR process, an enzymatic activity assay, or combinations thereof.

Methods and systems of the present disclosure provide an assay exhibiting increased selectivity and reduced limits of detection over traditional ELISA. The use of CBDs in the sandwich assays described herein bind directly to whole bacterial pathogens with a minimum of non-specific binding. Thus, little to no addition preparation of the sample is needed prior to testing for the presence of a target bacterial pathogen. The specificity also allows for multiplex detection which can be utilized in point-of-care diagnostics for rapid detection of pathogens. Further, the lack of non-specific binding means more reliable results with reduced false positives. Finally, the detection domains, e.g., the complexed enzymes, fluorescent material, or DNA, are highly sensitive, allowing for reliable detection even of trace amounts of a target bacterial pathogen.

EXAMPLES

Example 1: Preparation of Cell Wall Binding Domains

Biotin ligase (BirA) was amplified from pET21a-BirA with PCR premix (Promega, Madison, WI) and the PCR product was subcloned into a vector, pCDFDuet™-1™ (Novagen, Madison, WI), using In-Fusion® HD cloning kit (Clontech, Mountain View, CA) after cutting with NdeI to construct pCDF-BirA. After digesting pCDF-BirA with EcoRI, the Avi-tagged enhanced green fluorescent protein (Avi-EGFP) coding fragment was amplified from pT2KXIGdeltaIn-MCS-Avi-EGFP-rpl10a (Addgene 58380) and subcloned into pCDF-BirA using In-Fusion® cloning reaction to construct pHis-Avi-EGFP-BirA. The genes encoding $CBD^{SA}$ (G139-K246 region of lysostaphin), $CBD^{BA}$ (G171-K245 region of AmiBA2446) and $CBD^{LI}$ (N146-K289 region of Ply500) were amplified from the plasmids carrying the corresponding genes encoding lysostaphin, AmiBA2446, and ply500, respectively. Each amplified CBD was subcloned into the pCDF-Avi-EGFP-BirA digested with SalI to construct pHis-Avi-EGFP-CBD-BirA. The primers are listed in FIG. 4 (see SEQ ID NoS: 1-10).

To express biotinylated CBDs, E. coli BL21 (DE3) competent cells were transformed with a plasmid carrying the genes encoding both BirA and each of 6×His-Avi-EGFP-CBDs, where CBD represents $CBD^{BA}$, $CBD^{BA}$, and $CBD^{LI}$, respectively. The overnight cultures of E. coli, transformed with each plasmid and grown in an LB-streptomycin selection medium, were sub-cultured at a 1:20 ratio in LB and propagated to an OD600 nm of ~0.5. IPTG (400 μM) and biotin (50 μM) were then added for the simultaneous gene induction and in vivo biotinylation. After culturing the recombinant E. coli cells overnight at room temperature, cells were pelleted by centrifuging (3500 rpm) at 4° C. for 20 min. Cell pellets were suspended in native purification buffer containing 1 mM phenylmethylsulfonyl fluoride (PMSF) and 500 mM NaCl in 50 mM Tris buffer (pH 7.2). The cell suspension was incubated with lysozyme (100 μg/mL) and DNase (10 μg/mL) at 4° C. for 30 min. Cell suspensions were subjected to freeze-thaw cycles three times, followed by sonication to prepare cell lysates. The recombinant protein in the supernatant was purified using Ni-NTA affinity chromatography (Gold Biotechnology, St. Louis, MO). The bound protein was eluted by using native purification buffer containing 250 mM imidazole, and was dialyzed against Tris-buffered saline (TBS) containing 1 mM dithiothreitol (DTT) at pH 7.4 using a 3.5 kDa molecular weight cut-off filter. The protein concentrations were determined by using Micro BCA' Protein Assay Kit (ThermoFisher, Waltham, MA, USA). Protein expression and purification were monitored by 12% sodium dodecyl sulfate-polyacrylamide gel electrophoresis (SDS-PAGE) analysis.

Example 2: Preparation of Bacterial Pathogen Detection Complex Including Enzyme

To prepare $CBD-SA-GO_x$ complexes, biotin-$GO_x$ was first prepared. 5 mg of $GO_x$ was dissolved in 1 mL of sodium phosphate buffer (pH 7.0), and an excess amount of NHS-biotin (2 mM) was added (the molar ratio of biotin to $GO_x$ was ~20). The resulting mixture was stored at 4° C. overnight to achieve good coupling between biotin and $GO_x$. Excess free biotin-NHS was then removed with a desalting spin column. Biotin-CBD (20 μM) was mixed with 10 μM streptavidin (SA) and incubated at room temperature for 1 h to obtain the CBD-SA complex. The CBD-SA complex was then mixed with biotin-$GO_x$ (20 μM) and incubated at room temperature for 1 h to obtain the $CBD-SA-GO_x$ complex. The self-assembly of added proteins was confirmed by a blue native-PAGE kit (ThermoFisher, Waltham, MA, USA).

To establish the CBD-based sandwich assay for the detection of target bacterial pathogens, biotin-CBDs were immobilized on a neutravidin-coated 96-well plate (ThermoFisher, Waltham, MA, USA) by incubating 50 μL of various biotin-CBDs (20 μM in TBS) at room temperature for 1 h. The CBD-coated wells were then washed with phosphate buffered saline (PBS) after blocking the wells by adding free biotin (1 mM) and 1% BSA. The CBD coated plate was filled with 100 μL of test samples including target bacterial pathogens and negative controls (no bacteria for determining LOD and non-target bacteria in the case of multiplex assays), incubated at room temperature for 1 h, and then washed three times with PBS. The $CBD-SA-GO_x$ complexes (50 μL of 20 μM CBD) were added and incubated at room temperature for 1 h to form the sandwich with target bacterial pathogens. After washing the plate three times with PBS, 50 μL of glucose (10 mM) was added and incubated at room temperature for 1 h, and 20 μL of the reaction solutions were analyzed for the formation of hydrogen peroxide with the Pierce™ Quantitative Peroxide Assay Kits (ThermoFisher). To perform multiplex detection of different mixture of test bacterial pathogens in a 96-well plate, three different CBD sandwich pairs including biotin-CBDs ($CBD^{BA}$, $CBD^{BA}$, and $CBD^{LI}$) and their corresponding $CBD-SA-GO_x$ complexes were used.

Figure 5A:
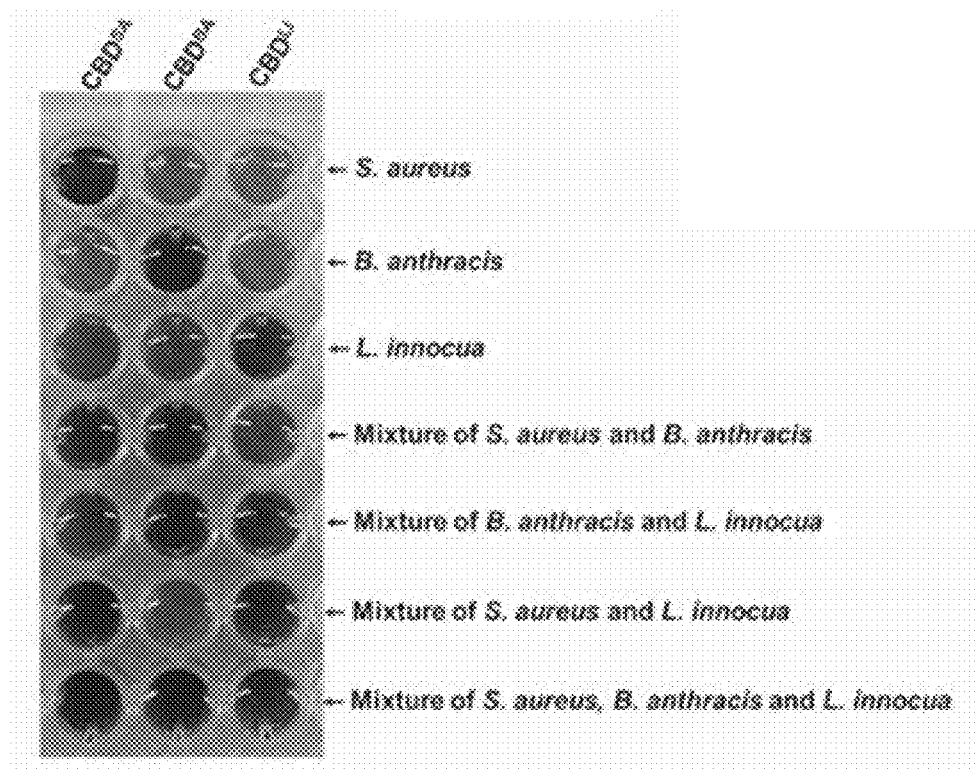
FIGS. 5A and 5B portray representative assay results using the bacterial pathogen detection systems and methods according to some embodiments of the disclosed subject matter.
Figure 5B:
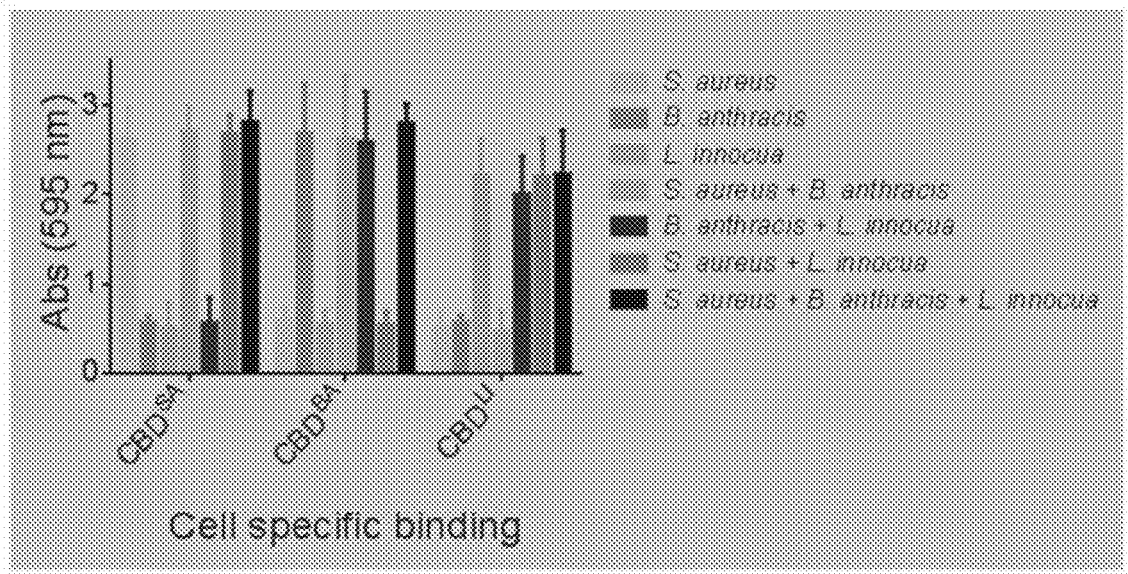

Following this protocol, multiplex detection of target bacteria was performed in synthetic mixtures of S. aureus, B. anthracis, and L. innocua spiked into PBS solution. The test bacteria were added to the PBS at about $10^6$ CFU/mL to demonstrate proof of concept and ensure a sufficient signal to noise (S/N) ratio. A series of bacterial suspensions were prepared, including the three individual bacteria separately, their two-component mixtures, and the three bacteria together. Referring now to FIGS. 5A and 5B, the specific CBDs could selectively capture and detect a target bacterial pathogen in the test samples containing a single bacterium or a mixture of bacteria in a single assay run. The existence of *B. anthracis* cells in seven different test samples was clearly identified with the $CBD^{BA}$-coated wells and the S/N ratios were over 4.0 (FIG. 5B). Similarly, the presence of *S. aureus* and *L. innocua* cells was identified only in the corresponding $CBD^{SA}$ and $CBD^{L1}$ regions, respectively. When the target cells were present in a mixture, their presence could be identified. In addition, and referring now to FIG. 6, the response of the detection assay was not impacted by the presence of non-target bacteria in a mixture. The ratios of absorbance (normalized by the S/N ratio) were essentially unchanged between the individual bacterium measurement and the measurement of that specific bacterium in a mixture. This was the case for all three bacteria tested.

After demonstrating the multiplex detection of three test bacteria, the LOD of the individual test bacteria was investigated via the CBD-based sandwich protocol. Correlation curves were obtained between cell suspension absorbance (600 nm) and cell concentration (CFU/mL). To determine the LOD, each target bacteria was serially diluted and bound to different numbers of test bacteria onto CBD coated 96-well plates. The $CBD-SA-GO_x$ complexes were then incubated for 1 h with their corresponding target bacteria to obtain LOD values using the CBD-based sandwich protocol. The LOD for *S. aureus* and *B. anthracis* in PBS solution was ~$10^3$ CFU/mL, but that of *L. innocua* was ~$10^4$ CFU/mL. Because of the non-specific binding of $CBD-SA-GO_x$, it was found that the cut-off signal of negative controls was ~0.5, which corresponds to ~10 pM of $GO_x$.

Example 3: Preparation of Bacterial Pathogen Detection Complex Including DNA

Several biotin-DNA barcodes (see FIG. 7 and SEQ ID NOS: 11-13) were prepared by PCR using forward 5'-biotinylated primers and reverse primers (see FIG. 8 and SEQ ID NOS: 14-25). To construct the CBD-SA-DNA complexes, the CBD-SA complex was first obtained by mixing biotin-CBD (20 μM) with streptavidin (10 μM) at room temperature for 1 h, followed by mixing biotin-DNAs (20 μM) and incubating at room temperature for additional 1 h to obtain three CBD-SA-DNA complexes including $CBD^{SA}$-SA-DNA-I, $CBD^{BA}$-SA-DNA-II, and $CBD^{L1}$-SA-DNA-III.

Three biotin-DNA barcodes were assembled with CBD-SA to construct CBD-SA-DNA complexes. Because the binding of the CBD to a target bacterium is highly strain-specific, specific DNA barcodes can be labeled on the surface of target bacterium. To apply the CBD-SA-DNA complexes to whole bacteria detection, complete removal of unconjugated biotin-DNAs and unbound CBD-SA-DNA complexes is important because of the extreme sensitivity of qPCR assay. The detection of DNA is extremely sensitive because a single DNA molecule can be detected through the PCR amplification and sequence-specific DNA barcodes enables highly selective multiplex PCR assays. While previous approaches employed PCR in both cell-specific selectivity and cell number detection, in the present example PCR was used just for detection while using CBDs for bacterial selectivity.

To establish the protocol for detecting whole-cell bacteria using CBD-SA-DNA complexes, the CBD-SA-DNA complexes were bound to target *S. aureus*, *B. anthracis*, and *L. innocua* cells for 30 min. The unbound CBD-SA-DNA complexes were removed using 0.22 μm centrifuge tube filters (Corning Costar spin-X from Sigma-Aldrich) by repeated (3×) centrifugal filtration and the bacterial cells bound to CBD-SA-DNA complexes were recovered by reversing the direction of the filter membrane. With removal of unbound CBD-SA-DNA complexes, no qPCR signal detection from the negative control (no bacterial cells) was identified.

The DNA barcodes on the surface of target bacterial cells were used as templates for the single or multiplex qPCR assay with target specific primers.

Figure 9:
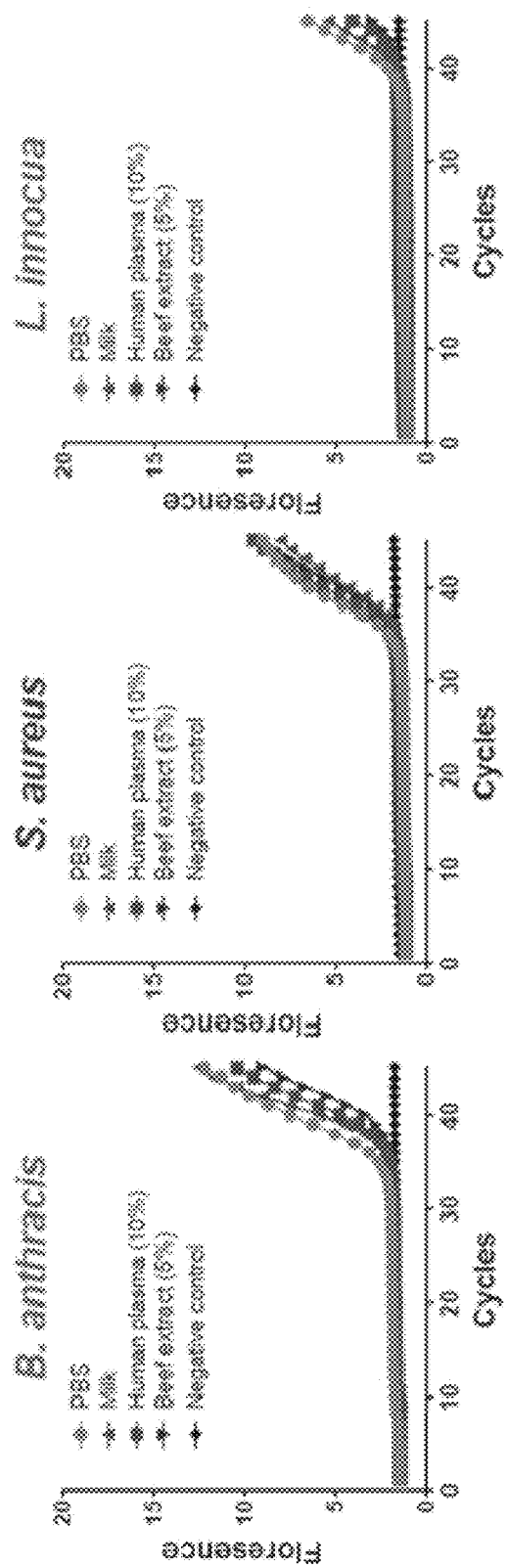
FIG. 9 portrays the binding specificity of the CBD complex to specific bacteria under various conditions.

To address a more complex, real-world environment, multiplex detection of target bacteria in reconstituted skim milk using CBD-SA-DNA complexes was performed. Various combinations of bacterial cell mixtures (5 CFU/mL of *B. anthracis*, 7 CFU/mL of *S. aureus*, and 10 CFU/mL of *L. innocua* cells) were prepared in milk, followed by cell recovery using 0.22 μm centrifuge tube filters. Three different CBD-SA-DNA complexes were then added on top of the centrifuge tube filters and let sit for 30 min to enable specific binding of each DNA barcode to its target bacterium. After removing the unbound DNAs via washing three times with PBS using the 0.22 μm centrifuge tube filters, the DNA barcodes bound to cells were recovered and used as templates for qPCR. The specific CBD made it possible to attach a specific DNA barcode onto the surface of a target bacterium. In addition to the detection in milk, target bacteria were found detectable in other settings, such as human plasma and beef extract with the LOD of <10 CFU/mL (see FIG. 9). Furthermore, there was no cross-reactive signal due to both the contamination of unbound DNAs and the non-specific binding of CBD-SA-DNA complexes. The specific binding of the $CBD^{SA}$-SA-DNA complex to sphere-shaped *S. aureus* cells in the mixture of various rod-shaped bacterial strains including *B. anthracis*, *B. subtilis*, *L. innocua*, *E. coli*, and *P. putida* cells was identified. As low as 2 CFU/mL was detected by this method. Therefore, systems and methods of the present disclosure are capable of identifying the presence of single bacterium or mixtures of bacteria in the various test samples with a single qPCR assay run.

Although the disclosed subject matter has been described and illustrated with respect to embodiments thereof, it should be understood by those skilled in the art that features of the disclosed embodiments can be combined, rearranged, etc., to produce additional embodiments within the scope of the invention, and that various other changes, omissions, and additions may be made therein and thereto, without parting from the spirit and scope of the present invention.

What is claimed is:

1. A bacterial pathogen detection complex comprising:
a lysin-derived cell wall binding domain;
a detection domain configured to produce a signal for detection; and
a linker complexed between the cell wall binding domain and the detection domain,
wherein the detection domain includes one or more DNA amplicons configured for use in a polymerase chain reaction process,
wherein at least one of the DNA amplicons form a DNA barcode specific to a target bacterial pathogen.

2. The complex according to claim 1, wherein the lysin-derived cell wall binding domain is derived from a cell wall binding domain from an endolysin, autolysin, bacteriocin, or exolysin, and is configured to bind a cell wall of the target bacterial pathogen.

3. The complex according to claim 1, wherein the lysin-derived cell wall binding domain is configured to selectively bind to members of the genus *Staphylococcus, Bacillus, Listeria, Streptococcus, Lactobacillus, Mycobacterium, Enterococcus, Pneumococcus, Salmonella, Campylobacter, Escherichia, Vibrio, Shigella, Pseudomonas*, or *Clostridia*.

4. The complex according to claim 1, wherein the lysin-derived cell wall binding domain is derived from lysostaphin, SA1, AmiBA2446, Ply500, Cpl-1, CD11, CDG, plyG, PlyC, CD27L, LysA, gp36, gp16, gp3, HydH5, CwlT, At1L, enerolysin A, Helviticin J, Millericin B, or mutanolysin.

5. The complex according to claim 1, wherein at least one of the lysin-derived cell wall binding domain and the detection domain are biotinylated.

6. The complex according to claim 5, wherein the linker is an avidin linker.

7. A bacterial pathogen detection kit comprising:
a surface including an avidin layer;
a first biotinylated lysin-derived cell wall binding domain complexed with the avidin layer to substantially immobilize the first biotinylated lysin-derived cell wall binding domain with respect to the surface; and
a first bacterial pathogen detection complex including:
a second biotinylated lysin-derived cell wall binding domain;
a detection domain; and
an avidin linker complexed between the cell wall binding domain and the detection domain,
wherein the detection domain includes a first DNA amplicon configured for use in a polymerase chain reaction process,
wherein the first DNA amplicon forms a DNA barcode specific to a first target bacterial pathogen.

8. The kit according to claim 7, wherein the first and second lysin-derived cell wall binding domains are derived from a cell wall binding domain from an endolysin, autolysin, bacteriocin, or exolysin, and are configured to bind a cell wall of the first target bacterial pathogen.

9. The kit according to claim 8, wherein the first and second lysin-derived cell wall binding domains are configured to selectively bind to members of the genus *Staphylococcus, Bacillus, Listeria, Streptococcus, Lactobacillus, Mycobacterium, Enterococcus, Pneumococcus, Salmonella, Campylobacter, Escherichia, Vibrio, Shigella, Pseudomonas*, or *Clostridia*.

10. The kit according to claim 8, wherein the first and second lysin-derived cell wall binding domains are derived from lysostaphin, SA1, AmiBA2446, Ply500, Cpl-1, CD11, CDG, plyG, PlyC, CD27L, LysA, gp36, gp16, gp3, HydH5, CwlT, At1L, enerolysin A, Helviticin J, Millericin B, or mutanolysin.

11. The kit according to claim 7, further comprising:
a third biotinylated lysin-derived cell wall binding domain complexed with the avidin layer; and
a second bacterial pathogen detection complex including a fourth biotinylated lysin-derived cell wall binding domain,
wherein the third and fourth biotinylated lysin-derived cell wall binding domain are configured to bind a cell wall of a second target bacterial pathogen,
wherein the second bacterial pathogen detection complex includes a second DNA amplicon configured for use in a polymerase chain reaction process,
wherein the second DNA amplicon forms a DNA barcode specific to the second target bacterial pathogen.

12. The kit according to claim 7, wherein the avidin linker is an avidin, streptavidin, neutravidin, or captavidin.

* * * * *